(12) United States Patent
Grisenti et al.

(10) Patent No.: US 9,765,082 B2
(45) Date of Patent: Sep. 19, 2017

(54) CRYSTALLINE FORM OF TIOTROPIUM BROMIDE WITH LACTOSE

(71) Applicant: EUTICALS SPA, Milan (IT)

(72) Inventors: Paride Grisenti, Milan (IT); Maria Argese, Sedriano (IT); Roberto Scrocchi, Pavia (IT); Alessandro Livieri, Pavia (IT); Giuseppe Guazzi, Milan (IT)

(73) Assignee: EUTICALS SPA, Milan (IT)

( * ) Notice: Subject to any disclaimer, the term of this patent is extended or adjusted under 35 U.S.C. 154(b) by 0 days.

(21) Appl. No.: 15/244,122

(22) Filed: Aug. 23, 2016

(65) Prior Publication Data

US 2017/0044176 A1    Feb. 16, 2017

Related U.S. Application Data

(63) Continuation of application No. PCT/EP2015/054091, filed on Feb. 26, 2015.

(30) Foreign Application Priority Data

Feb. 27, 2014 (EP) .................. 14157027

(51) Int. Cl.
  *A61K 31/439* (2006.01)
  *A61K 45/06* (2006.01)
  *C07D 491/08* (2006.01)
  *C07D 451/10* (2006.01)

(52) U.S. Cl.
  CPC .......... *C07D 491/08* (2013.01); *A61K 31/439* (2013.01); *A61K 45/06* (2013.01); *C07D 451/10* (2013.01); *C07B 2200/13* (2013.01)

(58) Field of Classification Search
  CPC ..... C07D 491/08; A61K 31/439; A61K 45/06
  See application file for complete search history.

(56) References Cited

U.S. PATENT DOCUMENTS

2011/0257215 A1* 10/2011 Watt .................. C07D 451/10
                                                       514/291

FOREIGN PATENT DOCUMENTS

WO    2009007687    1/2009

OTHER PUBLICATIONS

International Search Report issued in related application PCT/EP2015/054091 dated Apr. 1, 2015.
Bond, "What is a co-crystal?", CrystEngComm, 2007, 9, pp. 833-834.

* cited by examiner

*Primary Examiner* — Anoop Singh
*Assistant Examiner* — Doan Phan
(74) *Attorney, Agent, or Firm* — Stradley Ronon Stevens & Young, LLP

(57) ABSTRACT

A cocrystal of tiotropium bromide and lactose monohydrate is herein disclosed. In the cocrystal the components tiotropium bromide and lactose are preferably present in an almost stoichiometric ratio. Said cocrystal has a single endothermic event at about 191-193° C. determined by DSC. A process for the preparation of the cocrystal is also disclosed. Preferably, the cocrystal has a particle size distribution of D90<10 μm. The cocrystal is also disclosed for use as medicament, in particular for the treatment of a respiratory complaint, such as chronic obstructive pulmonary disease (COPD), bronchitis, emphysema and asthma. A pharmaceutical composition comprising the cocrystal as active ingredient is also disclosed, in particular for administration by inhalation. In the latter case, said cocrystal has a mean particle size of 0.5 to 10 μm, preferably 1 to 6 μm, more preferably 1.5 to 5 μm.

21 Claims, 7 Drawing Sheets

CRYSTALLINE FORM OF TIOTROPIUM BROMIDE WITH LACTOSE

CROSS REFERENCE TO RELATED APPLICATION

This application is a continuation of International Application No. PCT/EP2015/054091, filed on Feb. 26, 2015, which claims priority to European Patent Application No. 14157027.5, the disclosures of which are incorporated herein by reference in their entirety.

FIELD OF THE DISCLOSURE

The present invention relates to a new solid state of Tiotropium Bromide, a process for preparing it and its use as medicament and as active ingredient in a pharmaceutical composition for the treatment of respiratory complaints, particularly for the treatment of chronic obstructive pulmonary disease (COPD), bronchitis, emphysema and asthma.

BACKGROUND TO THE INVENTION

Tiotropium bromide (compound identified by CAS registry number 136310-93-5) was described for the first time in 1991 by Boheringer Inghelheim (EP 0418716) and presents the following structural formula:

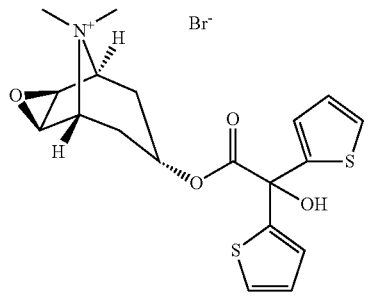 [SMILES: C[N+]1(C)[C@@H]2C[C@@H](OC(=O)C(O)(c3cccs3)c3cccs3)C[C@H]1[C@@H]1O[C@@H]12 ; [Br-]]

Tiotropium bromide is an anticholinergic bronchodilator with a long-lasting effect, 24 hours, which may be used to treat respiratory complaints, particularly COPD (chronic obstructive pulmonary disease), bronchitis, emphysema and asthma.

Tiotropium bromide is preferably administered by inhalation: suitable inhalable powders packed into appropriate capsules may be used (Spiriva®; U.S. Pat. Nos. 7,694,676 and 8,022,082) or alternatively, it may be administered by the use of inhalable aerosols (EP2201934).

The correct manufacture of the above mentioned compositions, suitable for the administration of a pharmaceutically active substance by inhalation, is based on the definition of physical parameters, like a particular crystalline form (see for example U.S. Pat. Nos. 6,608,055 and 677,423) and a defined particle size distribution (U.S. Pat. No. 7,070,800), which are connected with the nature of the active substance itself.

From literature data, Tiotropium Bromide is described to exist in different polymorphic forms as well as in an amorphous form. In more details, Tiotropium Bromide is described to exist in a crystalline monohydrate form (U.S. Pat. No. 6,777,423), in several anhydrous (U.S. Pat. No. 6,608,055, WO2006/117300, EP1682542) and solvate (U.S. Pat. No. 7,879,871, WO2010/101538, WO2011/015882) polymorphic forms. Some of these polymorphic forms are unstable and may change. For example, the monohydrate form described in U.S. Pat. No. 6,777,423 may be easily transformed after a mild heating at 40° C. for few hours into the corresponding anhydrous form described in U.S. Pat. No. 6,608,055.

Since the quality of a pharmaceutical formulation requires that an active substance should always have the same crystalline modification, the stability and properties of the crystalline active substance are subject to stringent regulatory requirements.

There is the need of a crystalline form of tiotropium bromide which is stable to humidity and to mechanical treatments, like the micronization or other milling techniques, and which meets the high demands mentioned above for any pharmaceutically active substance.

SUMMARY OF THE INVENTION

It has now surprisingly been found that a crystal modification of tiotropium bromide meeting the above requirements can be obtained in the form of a cocrystal with lactose. Unexpectedly, this cocrystal is stable towards the influence of moisture and humidity and to physical treatments like the micronization.

In the novel cocrystal the components tiotropium bromide and lactose are present in an almost stoichiometric ratio, as determined for example by NMR spectroscopy. Therefore, the present invention relates to a tiotropium bromide-lactose cocrystal in which the components tiotropium bromide and lactose are present, with the limit of resolution of the employed analytical technique (i.e. $^1$H-NMR), in a ratio of about 1:1.

This novel cocrystal is characterized by a single endothermic event at about 191-3° C. determined by DSC and by an X-Ray spectrum with characteristic 2theta values at 13.08; 14.16; 14.68; 17.90; 18.58; 19.06; 19.44; 21.02; 22.58; 23.24; 25.26; 26.20; 27.24; 28.08; 28.42; 29.96; 30.18; 31.80; 34.50; 34.82; 35.58; 38.70; 39.26; 41.52 and 50.06.

The present invention also relates to the cocrystal herein disclosed for use as a medicament, in particular for the treatment of respiratory complaints, particularly for the treatment of COPD and/or asthma.

The present invention also relates to a pharmaceutical composition comprising the above cocrystal as active ingredient.

The present invention also relates to a process for the preparation of the crystalline tiotropium bromide forms according to the present invention.

With a view to administration by inhalation, it is essential to provide the active substance in finely divided form. For this purpose, the cocrystal according to the invention is obtained in finely divided form using methods known in the prior art. Methods of micronizing active substances, like the air jet mill or the conical screen mill techniques, are known in the art. Preferably, after micronizing, the active substance has a mean particle size of 0.5 to 10 μm, preferably 1 to 6 μm, more preferably 1.5 to 5 μm.

Tiotropium bromide cocrystal according to the invention is particularly well suited to the preparation of, for example, pharmaceutical formulations for administration by inhalation such as inhalable powders or for example propellant-containing aerosol formulations, particularly inhalable powders and propellant-containing aerosol suspensions. These pharmaceutical formulations or compositions may contain in addition to the crystalline Tiotropium cocrystal according to the invention one or more additional active ingredients selected from the group consisting of betamimetics, EGFR inhibitors, PDEIV-inhibitors, steroids, and LTD4 antagonists, optionally together with a pharmaceutically acceptable excipients. It is intended that also other active ingredients can be added according to the general common knowledge.

The present invention will be now illustrated in detail, also by means of Figures and Examples.

DETAILED DESCRIPTION OF THE INVENTION

Figure 1:
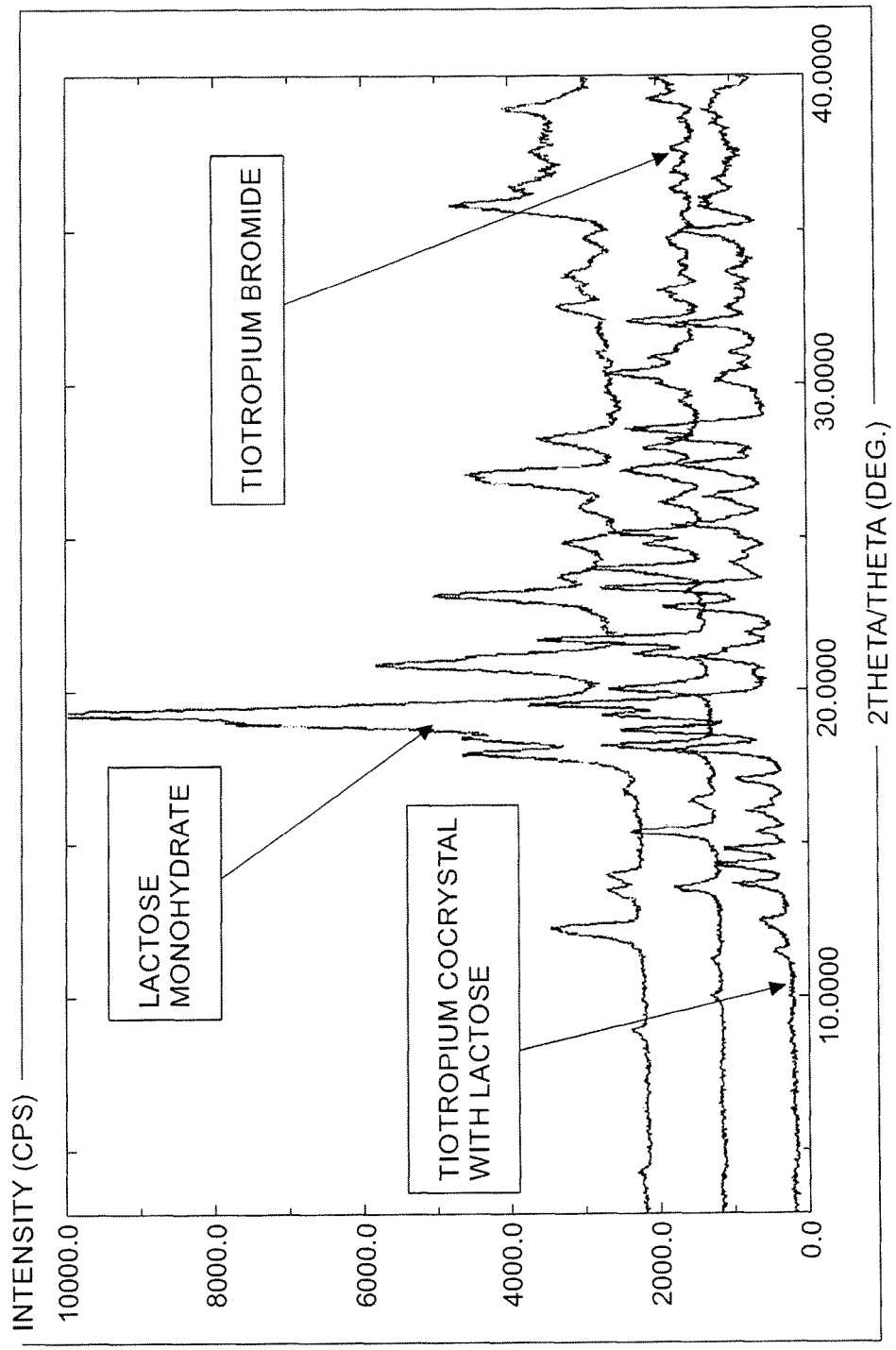
FIG. 1 shows a representative DRX spectrum of Tiotropium Bromide cocrystal with lactose (third DRX spectrum on the bottom) overlapped with the DRX spectra of the employed starting materials (from the top respectively the DRX spectra of lactose monohydrate and of Tiotropium Bromide).

Within the frame of the present invention, cocrystal are solids that are crystalline materials composed of two or more molecules in the same crystal lattice where each component is defined as either an atom, ion, or molecule (Stahly, G. P. (2009). "A Survey of Cocrystals Reported Prior to 2000". Crystal Growth & Design 9 (10): 4212; Regulatory Classification of Pharmaceutical Co-Crystals Edited by U.S. Department of Health and Human Services Food and Drug Administration Center for Drug Evaluation and Research (CDER) April 2013). Cocrystal exist in their neutral states and interact via nonionic interactions, as opposed to an ionic interaction, which would classify this crystalline solid as a salt form.

According to the present invention, the process for the preparation of Tiotropium Bromide lactose cocrystal comprises the following steps:
a) mixing Tiotropium Bromide and lactose in a relative molar ratio comprised between 1.0 and 1.3 in dimethylsulfoxide to a final concentration comprised between 1 and 14 M under stirring at room temperature to provide a suspension;
b) heating said suspension to obtain a solution;
c) adding portion wise under stirring to said solution, an aprotic organic solvent; preferably in a relative ratio, with respect to the dimethylsulfoxide, comprised between 7 and 9 times in volume;
d) cooling the reaction mixture under stirring to obtain a precipitate;
e) recovering said precipitate;
f) drying said precipitate under vacuum; and
g) optionally the dry product can be micronized.

In another embodiment of the present invention, the process for the preparation of the cocrystal herein disclosed further comprises after step e) and before step f) the following steps:

e') dispersing said precipitate from step e) in acetone to give a dispersion, and
e") recovering said precipitate from said dispersion and washing it with acetone, preferably about 5 volumes respect to the volume of employed dimethylsulfoxide.

The employed lactose in step a) can be in crystalline form monohydrate, anhydrous or amorphous, preferably in the monohydrate alpha crystalline form.

Preferably the temperature of heating said suspension in step b) is in a range of 50-55° C.

Preferably the aprotic organic solvent in step c) is selected among organic solvents with a log P value comprised between −0.24 and 1.14, like for example acetone, methylethylketone, ethylacetate, methyl acetate, n-propylacetate, more preferably acetone and ethyl acetate. Portion wise addition can be made according to normal experience, for example in a time ranging between few minutes and 2 hours, depending also on the operating conditions. A convenient timing is about 30'. This step is preferably carried out at 50-55° C.

Preferably the cooling rate in step d) is of about 1-2° C. per minute. The preferred temperature is of 20-25° C. and can be maintained for the desired time, typically for a time interval ranging from 0.5 to 5 hours, preferably from 1 to 4 hours, more preferably about 2 hours.

The steps e'), e") and g) can be performed optionally since they do not influence the solid state of the obtained crystalline form but only the chemical purity; alternatively the wet product obtained at point e) can be directly treated according to step f).

Recovery of the precipitate can be done with any conventional means, filtration being the preferred one.

The temperature range of step f) can be increased up to 60° C. without affecting the solid state of the obtained crystalline form. Typically, the drying temperature ranges around 20-40° C. Drying time can be selected according to normal experience, for example more than 24 hours, up to 96 hours, for example from 24 to 72 hours.

The step g) can be realized using conventional milling techniques like the Air Jet Mill technique or Conical screen mill without changes in the solid state; the preferred characteristic of the micronized product includes, but it is not limited to, particle size distribution with a D90<10 μm.

The cocrystal according to the present invention, in particular the cocrystal obtained by the process herein disclosed, is characterized by a single endothermic event at about 191-193° C. determined by DSC and by an X-Ray spectrum with characteristic 2theta values at 13.08; 14.16; 14.68; 17.90; 18.58; 19.06; 19.44; 21.02; 22.58; 23.24; 25.26; 26.20; 27.24; 28.08; 28.42; 29.96; 30.18; 31.80; 34.50; 34.82; 35.58; 38.70; 39.26; 41.52 and 50.06.

The stoichiometry of the components of the cocrystal of the present invention is about 1:1. The determination of the stoichiometry can vary around the ration of 1:1 depending on the analytical technique used. The ratio of the components can vary around the ratio of 1:1 on the condition that the stability of the cocrystal is not affected.

According to another object of the present invention, the cocrystal herein disclosed is for use as a medicament, in particular for the treatment of a respiratory complaint, more in particular chronic obstructive pulmonary disease (COPD), asthma, bronchitis and emphysema. The dosage, way of administration and clinical indication can be decided by the expert of the art, based on the general knowledge, for example as shown in EP 0418716 for aerosol and tablets. See also US 200211529, US 20030087927 and EP 2201934 for aerosol application.

Another object of the present invention is a pharmaceutical composition comprising the above cocrystal as an active ingredient. Pharmaceutical compositions according to the present invention are characterized by the presence of the cocrystal herein disclosed. Said compositions comprise any of conventional vehicles, excipients, formulative ingredients and can be prepared according to the general knowledge in this art. A general reference can be found for example in Remington "The Science and Practice of Pharmacy," 21$^{st}$ edition Pharmaceutical Press. In a preferred embodiment, said composition is suitable for administration by inhalation. In a more preferred embodiment, in said composition for inhalation, said cocrystal has a mean particle size of 0.5 to 10 μm, preferably 1 to 6 μm, and more preferably 1.5 to 5 μm.

Pharmaceutical compositions for inhalation, in particular for aerosol inhalation are well known in the art and do not need any specific description for the present invention, the general common knowledge being sufficient, see for example Pharmaceutical Inhalation Aerosol Technology, Anthony J. Hickley ed., Marcel Dekker, Inc. 2004.

Embodiments of the pharmaceutical compositions of the present invention comprise those compositions disclosed in U.S. Pat. Nos. 7,694,676 and 8,022,082, wherein the active ingredient is the cocrystal of the present invention.

The following Examples further illustrate the present invention.

Materials and Methods $^1$H NMR analyses were performed at 500 MHz with a Bruker FT-NMR AVANCE™ DRX500 spectrometer. Infrared spectra (IR) were registered on a Perkin Elmer instrument (Mod FTIR Spectrum one) equipped with universal ATR sampling. DSC were registered on a Perkin Elmer instrument (Mod. DSC7) at a heating rate of 10° C./min from 40° C. to 260° C. Between 3 and 6 mg of sample were used and all samples were crimped in hermetically sealed aluminum pans X-Ray Diffraction spectra were registered by means of diffractometer (Rigaku-D-Max) from a start angle [½ 2-theta] of 5.000 to 60.000. The diffraction diagrams were obtained employing a Cu anode (Kα=1,54060 Å and Kα=1, 54439 Å). The HPLC method utilized to check the quality of Tiotropium Bromide in the examined samples is the same as described in the European Pharmacopoeia 7.0.

EXAMPLE 1

Preparation of Tiotropium Bromide Cocrystal with Lactose in Dimethylsulfoxide and Acetone Tiotropium Bromide (4.25 g; 8.99 mmol) and lactose monohydrate (3.58 g; 9.9 mmol) were dispersed at room temperature in dimethylsulfoxide (7.2 ml). The mixture was heated under stirring at the temperature of 50-55° C. to obtain a limpid solution. Then acetone (55 ml) was added dropwise in 30' maintaining the reaction mixture under stirring at 50-55° C. The obtained solution was cooled down at 20-25° C. and kept at this temperature under stirring for 2 hours. After this period a suspension was obtained. The precipitate was recovered by suction and the wet product slurried in acetone (14.9 ml) under stirring for 90'. The product was recovered by filtration, washed on the filter with acetone (4 times with 8.5 ml each) and dried under vacuum at 40° C. for 48 hours to afford 6.76 g (8.11 mmol; 90% molar yields) of dry product.

The obtained crystals were analyzed by X-Ray powder diffraction (XRPD), differential scanning calorimetry (DSC), and $^1$H-NMR (500 MHz) indicating that a new crystalline form, namely a cocrystal of Tiotropiumbromide with lactose is formed.

A representative DRX spectrum of Tiotropium Bromide cocrystal with lactose is shown in FIG. 1 (third DRX spectrum from the bottom) overlapped with the DRX spectra of the employed starting materials (from the top respectively the DRX spectra of lactose monohydrate and of Tiotropium Bromide). The list of the characteristic diffraction peaks including normalized intensities of Tiotropium Bromide cocrystal is shown in table 1.

TABLE 1

| 2theta | Intensity | I/Io |
|---|---|---|
| 11.360 | 420 | 21 |
| 12.340 | 453 | 23 |
| 13.080 | 366 | 18 |
| 13.520 | 843 | 42 |
| 14.160 | 1026 | 51 |
| 14.680 | 1098 | 54 |
| 15.280 | 659 | 33 |
| 15.960 | 696 | 35 |
| 16.300 | 524 | 26 |
| 16.960 | 872 | 43 |
| 17.900 | 1472 | 73 |
| 18.580 | 1897 | 93 |
| 19.060 | 1847 | 91 |
| 19.440 | 1938 | 95 |
| 20.460 | 791 | 39 |
| 21.020 | 826 | 41 |
| 21.720 | 819 | 41 |
| 22.580 | 1712 | 84 |
| 23.240 | 2044 | 100 |
| 23.980 | 919 | 45 |
| 24.380 | 853 | 42 |
| 25.260 | 1499 | 74 |
| 26.200 | 1156 | 57 |
| 27.240 | 1240 | 61 |
| 28.080 | 1554 | 77 |
| 28.420 | 1935 | 95 |
| 29.960 | 1043 | 52 |
| 30.180 | 1024 | 51 |
| 30.500 | 819 | 41 |
| 30.900 | 924 | 46 |
| 31.800 | 1399 | 69 |
| 32.340 | 960 | 47 |
| 32.980 | 839 | 42 |
| 33.440 | 937 | 46 |
| 34.500 | 1032 | 51 |
| 34.820 | 1424 | 70 |
| 35.580 | 1196 | 59 |
| 36.380 | 899 | 44 |
| 36.880 | 964 | 48 |
| 37.220 | 917 | 45 |
| 37.740 | 913 | 45 |
| 37.960 | 982 | 49 |
| 38.700 | 1163 | 57 |
| 39.260 | 1035 | 51 |
| 39.880 | 833 | 41 |
| 41.520 | 1396 | 69 |
| 41.940 | 976 | 48 |
| 43.400 | 1005 | 50 |
| 43.600 | 989 | 49 |
| 44.900 | 1074 | 53 |
| 45.360 | 893 | 44 |
| 46.920 | 1001 | 49 |
| 47.480 | 932 | 46 |
| 48.060 | 958 | 47 |
| 49.540 | 1107 | 55 |
| 50.060 | 1023 | 51 |
| 51.820 | 995 | 49 |
| 54.440 | 990 | 49 |
| 55.220 | 946 | 47 |
| 56.340 | 960 | 47 |
| 58.100 | 926 | 46 |

The DSC-thermograms of the lactose cocrystal with Tiotropium bromide shows an endothermic event at ca.

Figure 2:
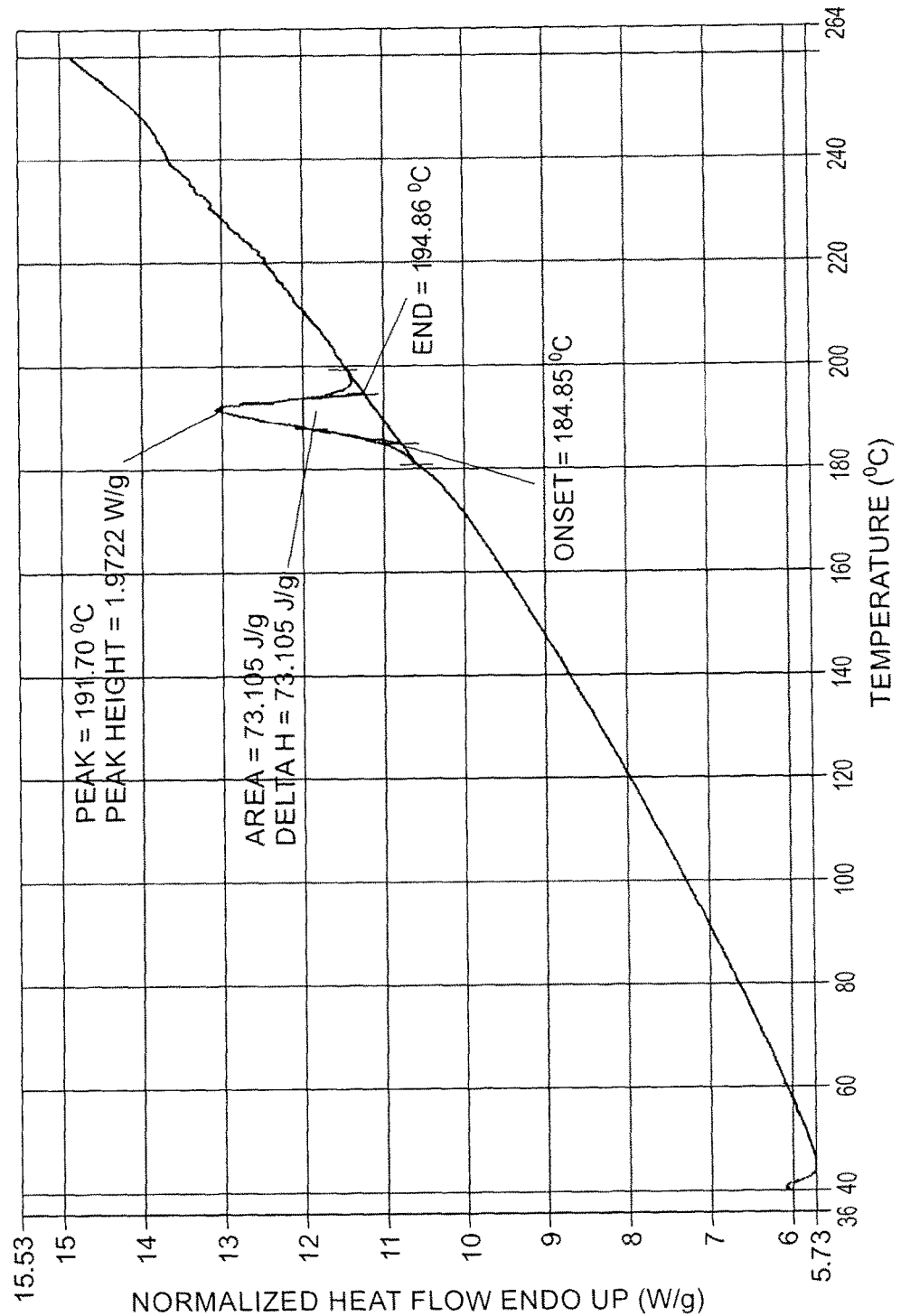
FIG. 2 shows the DSC-thermograms of the lactose cocrystal with Tiotropium bromide with an endothermic event at about 191-193° C.

191-193° C. indicating melting of this material. The obtained DSC-diagram is depicted in FIG. 2.

Figure 3:
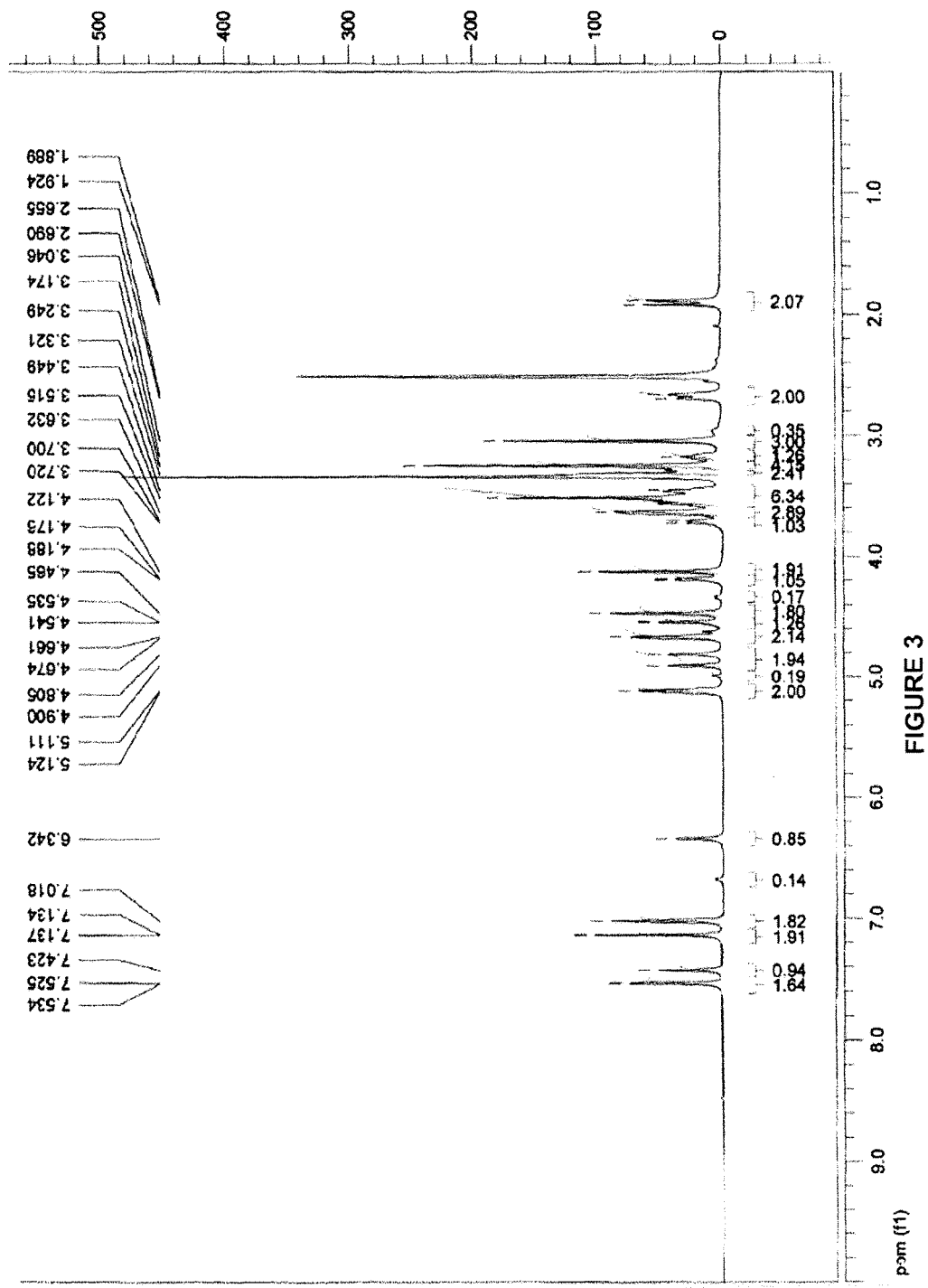
FIG. 3 shows $^1$H-NMR spectra (500 MHz) were recorded of the obtained cocrystal.
Figure 3A:
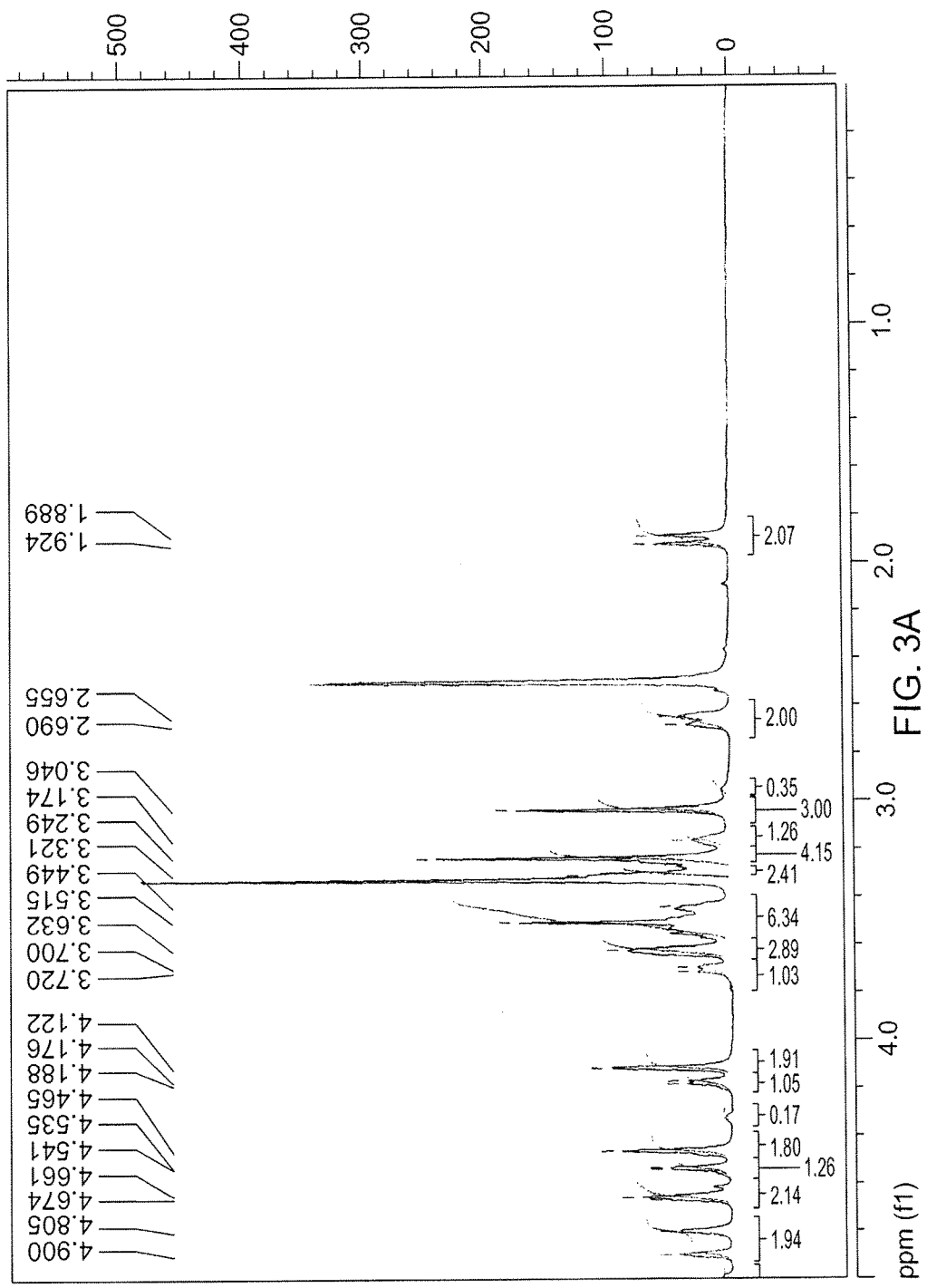
FIG. 3A shows expanded zone of the same sample from 0 to 5 ppm.

In order to get an idea on the stoichiometry of the obtained cocrystal, $^1$H-NMR spectra (500 MHz) were recorded. The samples were dissolved in d6-DMSO for analysis. The corresponding spectrum is shown in FIGS. 3 and 3A. In addition to the characteristic $^1$H-NMR signals of tiotropium there is a signal at 4.17 and 4.18 ppm which is indicative of H1' of lactose (integration 1H; ref Hyunnsook Ko et al. Bull. Korean Chem. Soc. 2005, Vol. 26, No. 12, 2001-6). Integration of this signal compared to the signal at 4.12 ppm of CH 1 and 5 (integration 2H; ref. Zhenguang Lin et al. Spectrochimica Acta Part A 75 (2010), 1159-1162) of Tiotropium shows that the cocrystal has a stoichiometry which is close to 1:1.

EXAMPLE 2

Preparation of Tiotropium Bromide Cocrystal with Lactose in Dimethylsulfoxide and Ethyl Acetate Tiotropium Bromide (2.0 g; 4.23 mmol) and lactose monohydrate (1.68 g; 4.66 mmol) were dispersed at room temperature in dimethylsulfoxide (3.4 ml). The mixture was heated under stirring at the temperature of 50-55° C. to obtain a limpid solution. Then ethylacetete (48 ml) was added dropwise in 30' maintaining the reaction mixture under stirring at 50-55° C. The obtained solution was cooled down at 20-25° C. and kept at this temperature under stirring for 2 hours. After this period the product was recovered by filtration, washed on the filter with ethyl acetate (4 times with 5 ml each) and dried under vacuum at 20° C. for 48 hours to afford 2.83 g (3.39 mmol; 80% molar yields) of dry product.

The physio-chemical data of the obtained solid are the same of the product isolated in the Example 1.

Stability Data of the Crystalline Form of Tiotropium Bromide Cocrystal with Lactose Tiotropium Bromide Cocrystal obtained according to the Example 1 was analyzed by DRX (powder) at 1, 2 and 3 months in the following storage conditions in order to verify the stability of this crystalline form. The results are shown in Table 2.

TABLE 2

| Primary packaging | 1st month | 2nd month | 3rd month |
|---|---|---|---|
| Amber glass at 25° C. | Unchanged | Unchanged | Unchanged |
| Amber glass at 40° C. | Unchanged | Unchanged | Unchanged |
| Polyethylene bag 25° C./ 60% UR | Unchanged | Unchanged | Unchanged |

Figure 4:
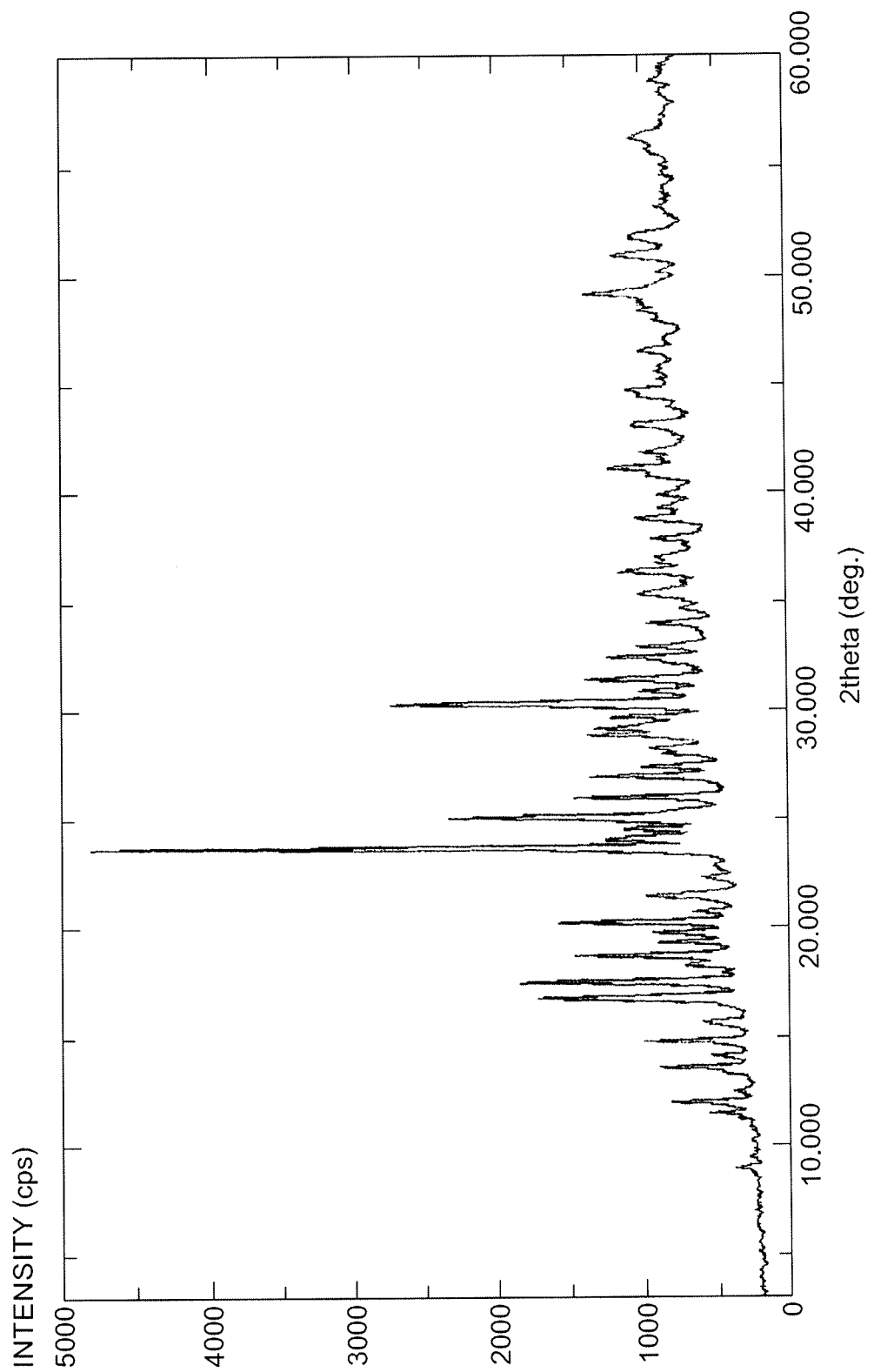
FIGS. 4 and 4A show the DRX spectra of a Tiotropium Bromide monohydrate before and after the heating at 40° C. at 50% UR for 72 hours.
Figure 4A:
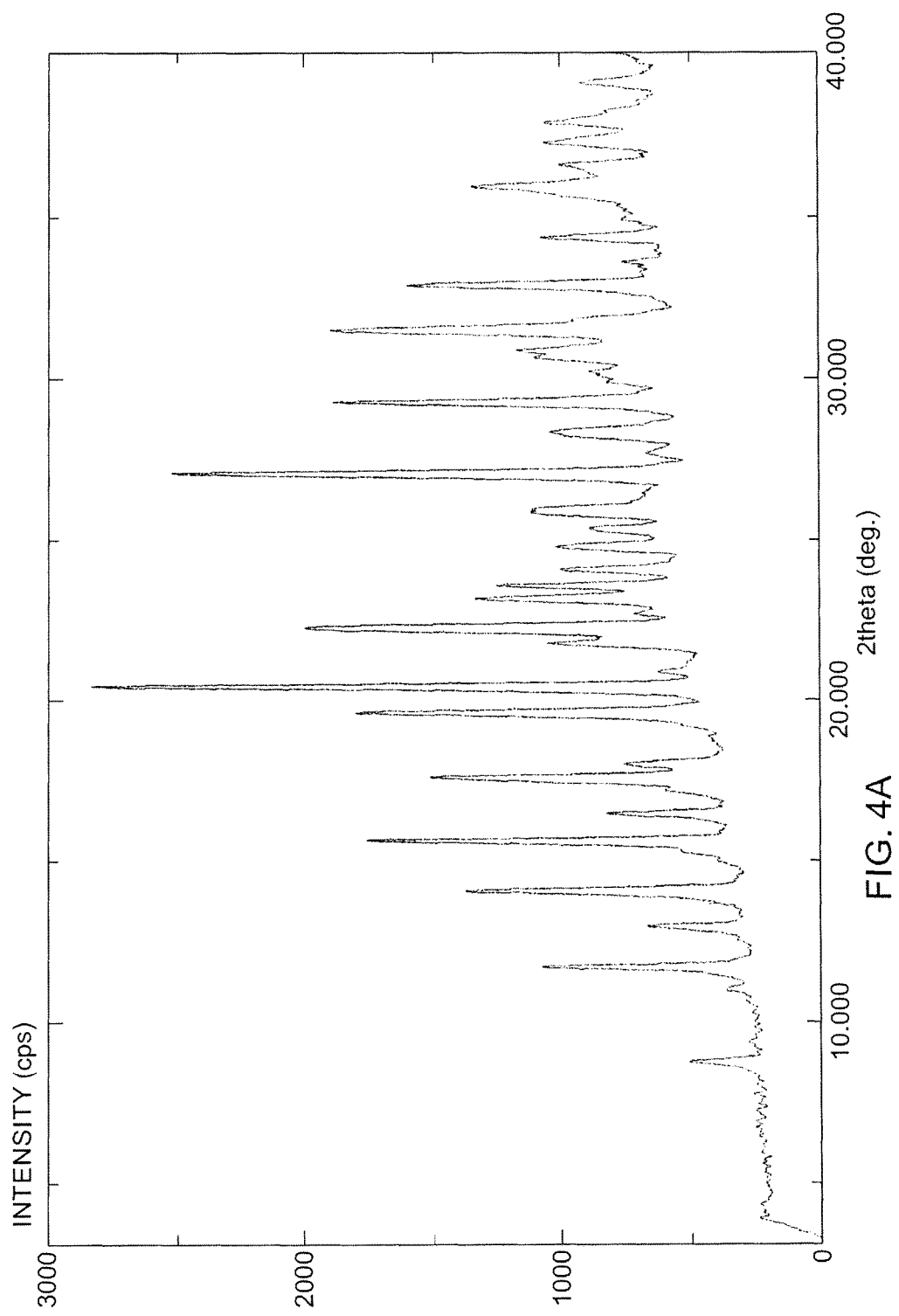

In the same storage conditions, and particularly using as primary packaging polyethylene bag, Tiotropium Bromide may absorb or lose water, thus changing the crystalline form. In fact, this is an equilibrium that is driven by the relative humidity of the environment. This change in the solid state can be nearly quantitative: so for example the hydrate form described in U.S. Pat. No. 6,777,423 changes into the corresponding anhydrous form described in U.S. Pat. No. 6,608,055 after heating at 40° C. at 50% UR for 72 hours. See the enclosed DRX spectra of a Tiotropium Bromide monohydrate before and after the above described treatment (FIGS. 4 and 4A).

Micronization of Tiotropium Bromide Cocrystal with Lactose

Figure 5:
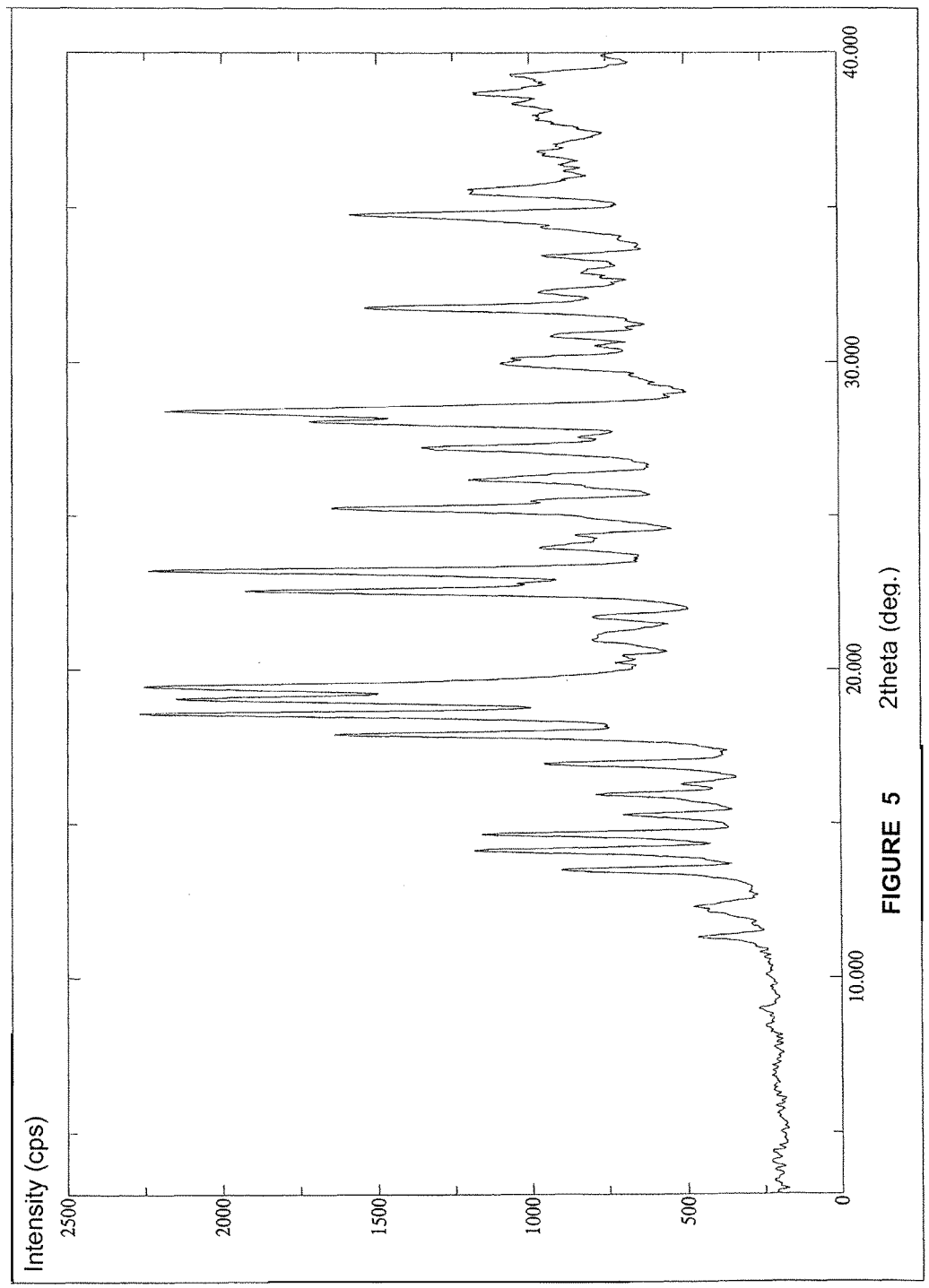
FIG. 5 shows DRX data of Tiotropium Bromide cocrystal with lactose micronized using air jet mill technique.

A sample of Tiotropium Bromide Cocrystal obtained according to Example 1 was micronized using the air jet mill technique in order to verify if this physical treatment affected the quality and the solid state of this product. The obtained analytical results (particle size distribution and chemical purity determined by HPLC) are shown in Table 3; the DRX data of the micronized material confirm that the solid state is not changed after micronization (FIG. 5).

TABLE 3

| | D10 | D50 | D90 | HPLC purity of Tiotropium Bromide |
|---|---|---|---|---|
| Unmilled Cocrystal | 2.03 microns | 16.6 microns | 178 microns | 99.91% |
| Milled Cocrystal | 0.67 microns | 1.95 microns | 5 microns | 99.88% |

The invention claimed is:

1. A cocrystal of tiotropium bromide and lactose.

2. The cocrystal of claim 1, wherein the tiotropium bromide and the lactose are present in a 1:1 to 1:1.3 stoichiometric ratio.

3. The cocrystal of claim 1, wherein said lactose comprises a form selected from the group consisting of monohydrate, anhydrous and amorphous.

4. The cocrystal of claim 3, wherein the lactose is in a monohydrate alpha crystalline form.

5. The cocrystal of claim 1, wherein the cocrystal undergoes a single endothermic event at about 191-193° C. determined by differential scanning calorimetry.

6. The cocrystal of claim 1, characterized by X-Ray spectrum with characteristic 2theta values at 13.08; 14.16; 14.68; 17.90; 18.58; 19.06; 19.44; 21.02; 22.58; 23.24; 25.26; 26.20; 27.24; 28.08; 28.42; 29.96; 30.18; 31.80; 34.50; 34.82; 35.58; 38.70; 39.26; 41.52 and 50.06.

7. A pharmaceutical composition comprising the cocrystal of claim 1 as an active ingredient and one or more conventional vehicles, excipients, or formulative ingredients.

8. The pharmaceutical composition of claim 7, wherein the pharmaceutical composition is suitable for administration by inhalation and the cocrystal has a mean particle size of 0.5 to 10 μm.

9. The pharmaceutical composition of claim 8 wherein the cocrystal has a mean particle size of 1 to 6 μm.

10. The pharmaceutical composition of claim 8 wherein the cocrystal has a mean particle size of 1.5 to 5 μm.

11. The pharmaceutical composition of claim 7, further comprising an additional active ingredient.

12. The pharmaceutical composition according to claim 11, wherein the additional active ingredient is a betamimetic, an EGFR inhibitors, a PDEIV-inhibitor, a steroid, or an LTD4 antagonist.

13. A method for treating a respiratory complaint, comprising administering the cocrystal of claim 1 to a subject in need of treatment for a respiratory complaint.

14. The method of claim 13, wherein said respiratory complaint is chronic obstructive pulmonary disease (COPD), asthma, bronchitis and emphysema.

15. A process for the preparation of a cocrystal of tiotropium bromide and lactose, comprising the following steps:
    a) mixing tiotropium bromide and lactose in a relative molar ratio comprised between 1.0 and 1.3 in dimethylsulfoxide to a final concentration between 1 and 14 M under stirring at room temperature to provide a reaction mixture;

b) heating said reaction mixture under stirring at 55-50° C. to obtain a solution;
c) adding portionwise under stirring at 55-50° C. to said reaction mixture, an aprotic organic solvent in a relative ratio, with respect to the dimethylsulfoxide, comprised between 7 and 9 times in volume;
d) cooling down the reaction mixture under stirring to 20-25° C. to obtain a precipitate, wherein said precipitate is the cocrystal of tiotropium bromide and lactose;
e) recovering said precipitate; and
f) drying said precipitate under vacuum.

16. The process according to claim 15, wherein said lactose comprises a form selected from the group consisting of monohydrate, anhydrous and amorphous.

17. The process of claim 15, wherein the lactose is in the monohydrate alpha crystalline form.

18. The process of claim 15, further comprising the following steps after step e) and before step f):
e') dispersing said precipitate from step e) in acetone to give a dispersion, and
e") recovering said precipitate from said dispersion and washing said precipitate with acetone.

19. The process of claim 15, further comprising the following step after step f):
g) micronizing said dry precipitate to obtain a product with a particle size distribution of D90<10 μm.

20. The process of claim 15, wherein said aprotic organic solvent in step c) has a log P value comprised between −0.24 and 1.14.

21. The process of claim 15, wherein step d) comprises cooling down the reaction mixture at a cooling rate of about 1-2° C. per minute.

* * * * *